(12) United States Patent
Itsuji et al.

(10) Patent No.: US 6,684,686 B2
(45) Date of Patent: Feb. 3, 2004

(54) NON-CONTACT TYPE ATOMIC MICROSCOPE AND OBSERVATION METHOD USING IT

(75) Inventors: Takeaki Itsuji, Kanagawa (JP); Shunichi Shido, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 32 days.

(21) Appl. No.: 09/993,671

(22) Filed: Nov. 27, 2001

(65) Prior Publication Data

US 2002/0063213 A1 May 30, 2002

(30) Foreign Application Priority Data

Nov. 29, 2000 (JP) ........................................ 2000-362702
Nov. 13, 2001 (JP) ........................................ 2001-347392

(51) Int. Cl.[7] .......................... G01B 5/28; G01N 23/00
(52) U.S. Cl. ........................................................ 73/105
(58) Field of Search ........................... 73/105; 250/306, 250/307

(56) References Cited

U.S. PATENT DOCUMENTS

| | | | | |
|---|---|---|---|---|
| 5,440,121 A | * | 8/1995 | Yasutake et al. ............. | 250/306 |
| 5,631,410 A | * | 5/1997 | Kitamura ...................... | 73/105 |
| 5,907,096 A | * | 5/1999 | Chen ............................ | 73/105 |
| 5,955,660 A | * | 9/1999 | Honma ........................ | 73/105 |
| 6,005,246 A | * | 12/1999 | Kitamura et al. ............. | 73/105 |
| 6,073,485 A | * | 6/2000 | Kitamura ...................... | 73/105 |
| 6,079,254 A | * | 6/2000 | Chen et al. ................... | 73/105 |
| 6,097,197 A | * | 8/2000 | Matsuyama et al. ........ | 250/306 |
| 6,169,281 B1 | * | 1/2001 | Chen et al. ................... | 73/105 |
| 6,185,991 B1 | * | 2/2001 | Hong et al. ................... | 73/105 |
| 6,189,374 B1 | * | 2/2001 | Adderton et al. ............. | 73/105 |
| 6,196,061 B1 | * | 3/2001 | Adderton et al. ............. | 73/105 |
| 6,281,495 B1 | * | 8/2001 | Kitamura ...................... | 73/105 |

* cited by examiner

*Primary Examiner*—Daniel S. Larkin
(74) *Attorney, Agent, or Firm*—Fitzpatrick, Cella, Harper & Scinto (57) ABSTRACT

A non-contact-type atomic microscope including a plurality of probes differing in resonance frequency, an actuator for vibrating the plurality of probes simultaneously, and a drive signal generating circuit for generating a drive signal for the actuator. The drive signal contains a predetermined frequency for vibrating each of the plurality probes. Also, there is a method for observing a surface shape of a sample by using a plurality of probes. The method includes a step of vibrating the plurality of probes simultaneously with a common actuator in a vicinity of their resonance frequencies. A signal for driving the actuator contains a predetermined frequency for vibrating each of the probes.

7 Claims, 5 Drawing Sheets

NON-CONTACT TYPE ATOMIC MICROSCOPE AND OBSERVATION METHOD USING IT

BACKGROUND OF THE INVENTION

1. Field of the Invention

The present invention relates to a scanning probe microscope for observing the surface shape of a sample by detecting a physical interaction between a probe and the sample surface, and more particularly to a non-contact-type atomic microscope and an observation method for observing the sample surface in a non-contact mode by detecting atomic force.

2. Related Background Art

In recent years, since the development of the scanning tunneling microscope (STM) permitting direct observation of the electronic structures of conductors, microscope systems that can acquire various information items and their distribution pattern by scanning with a probe having a sharp tip including the atomic force microscope (AFM), the scanning capacitance microscope (SCaM) and the scanning near-field microscope (SNOM) have been developed one after another. Today these microscopes are generically known as scanning probe microscopes (SPM), and extensively used as means for observation of fine structures having resolutions on the atomic or molecular level.

Figure 6:
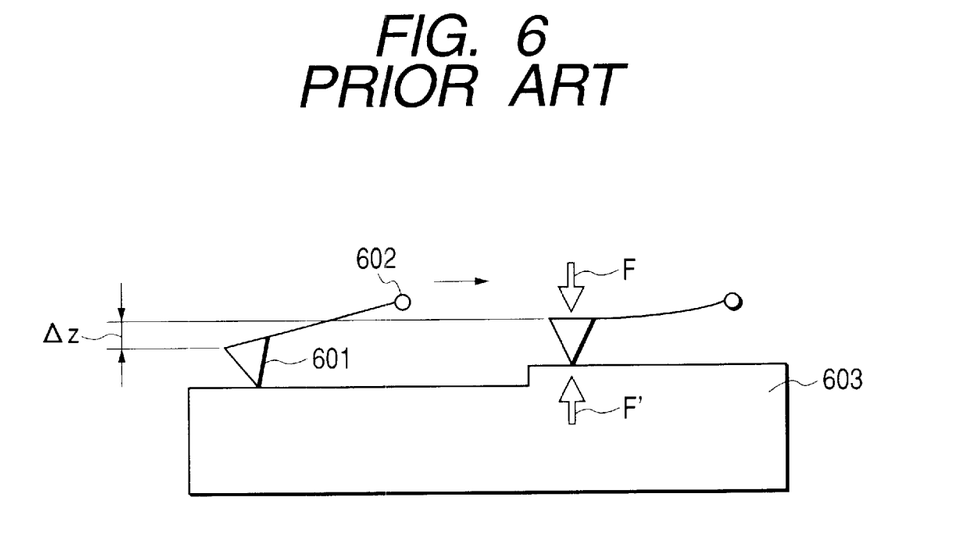
FIG. 6 illustrates the description of the principle of AFM observation.

Atomic force microscopy (AFM) is a technique of observing fine unevenness of the sample surface by detecting the quantity of flexure of the probe generated by atomic force in the contact region (repulsion region). FIG. 6 illustrates the principle of observation by AFM. In FIG. 6, a probe 601 is supported at a fulcrum 602, and scans the surface of a sample 603 in a prescribed direction. On a convex portion of the surface of the sample 603, a local force F (and a repulsion force F') works on the probe 601, resulting in a flexure $\Delta z$. Detection of the flexure $\Delta z$ in a certain manner allows observation of the fine unevenness of the surface of the sample. In this AFM observation, unlike scanning tunneling microscopy (STM) by which only conductor samples can be observed, insulator samples can also be readily observed, and accordingly it has a broad applicable range. For this reason, it is attracting note as a promising next generation technique for atomic and molecular manipulation, and many reports have been made in this regard.

However, AFM observation in the contact region as mentioned above would invite a change in the tip shape of the probe due to abrasion, and many findings on the adverse effects of such changes in tip shape have been reported. Furthermore, there is a risk of damaging the sample by the tip of the probe.

As a technique to permit observation of the shape of the sample surface without letting the tip of the probe come into physical contact with the sample surface, non-contact type atomic microscopy (ncAFM) is known. This ncAFM is a version of AFM by which the surface shape of the sample is observed by vibrating the probe at the frequency of or near its resonance point in the non-contact region (gravity region) and detecting variations in the resonance frequency of the probe due to the physical interaction between the sample surface and the probe (the atomic force working between the probe and the sample surface). The resonance point here means the point where the amplitude (vibration displacement) of the probe reaches its maximum when the probe is vibrated in a prescribed frequency range, and the frequency at that point is known as the resonance frequency. The resonance frequency varies with physical interactions between the sample and the probe. The detection sensitivity of the probe is at its highest when the probe is vibrated at its resonance point, and diminishes as it deviates from the resonance point.

As this ncAFM observation is carried out in the non-contact region, the influence of contact between the tip of the probe and the sample surface can be averted. For this reason, ncAFM is all the more expected to prove useful when applied to atomic or molecular manipulation.

This ncAFM is being improved for practical application with many objects including making the hardware more compact and increasing its speed of data processing (image processing of the surface shape of the sample). As one of such attempts, a non-contact atomic force microscope (ncAFM) for parallel (multiple) processing using a plurality of probes (multiprobe) to increase the data processing throughput has been developed. However, the use of a multiprobe involves the following problems.

It is difficult on account of manufacturing errors and other factors for all the multiple probes to have the same resonance point even if they are produced in the same manufacturing process. In ncAFM, as described above, since variations in the resonance frequency of a probe due to physical interactions between the sample surface and the probe surface that take place when the probe is vibrated at a frequency of or near its resonance point are to be detected, the multiple probes should be vibrated at a frequency of or near the resonance point of each.

The simplest way to vibrate each of multiple probes at a frequency of or near its resonance point is to provide a vibration actuator for each probe and vibrate the probe. In this case, however, equipping every probe with an actuator invites a large overall size of the system where a large number of probes are used, and the wiring of probe heads also becomes complex. In addition, it is necessary to tune the frequency of signals applied to each actuator to a frequency of or near its resonance point of each probe, and the time taken by this tuning of frequency would increase as the array of probes is expanded.

To prevent the system from becoming too large, it is conceivable to use a common actuator for all the multiple probes or each of groups into which the probes are divided and vibrate all the probes or the grouped probes at a common frequency (e.g. an average resonance frequency of the probes). In this case, however, some of the probes may prove less sensitive than others in detection on account of deviations of their resonance points due to manufacturing errors or the like, and some may even prove unusable for observation, making accurate observation of the sample surface impossible. These problems become more significant as the array of probes is expanded.

SUMMARY OF THE INVENTION

An object of the present invention is to provide a non-contact-type atomic microscope and an observation method solving the above-noted problem of unevenness of sensitivity among multiple probes, permitting accurate observation of a sample surface and contributing to reducing the system size and cost.

In order to achieve the object stated above, the invention offers the following configurations.

A non-contact-type atomic microscope comprising:

a plurality of probes differing in resonance frequency;

an actuator for vibrating the plurality of probes at the same time; and a drive signal generating circuit for generating a drive signal for the actuator containing a resonance frequency of each of the plurality of probes.

An observation method for observing a surface shape of a sample by using a plurality of probes, comprising:

a step of vibrating the plurality of probes at the same time with a common actuator near their resonance frequencies;

wherein a signal for driving the actuator contains the resonance frequency of each of the probes;

a step of detecting any displacement in each of the probes and generating an output signal; and a step of generating a signal representing the surface shape on the basis of the output signal.

Details will be given in embodiments described below.

DESCRIPTION OF THE PREFERRED EMBODIMENTS

Next will be described embodiments of the present invention with reference to drawings.

Figure 1:
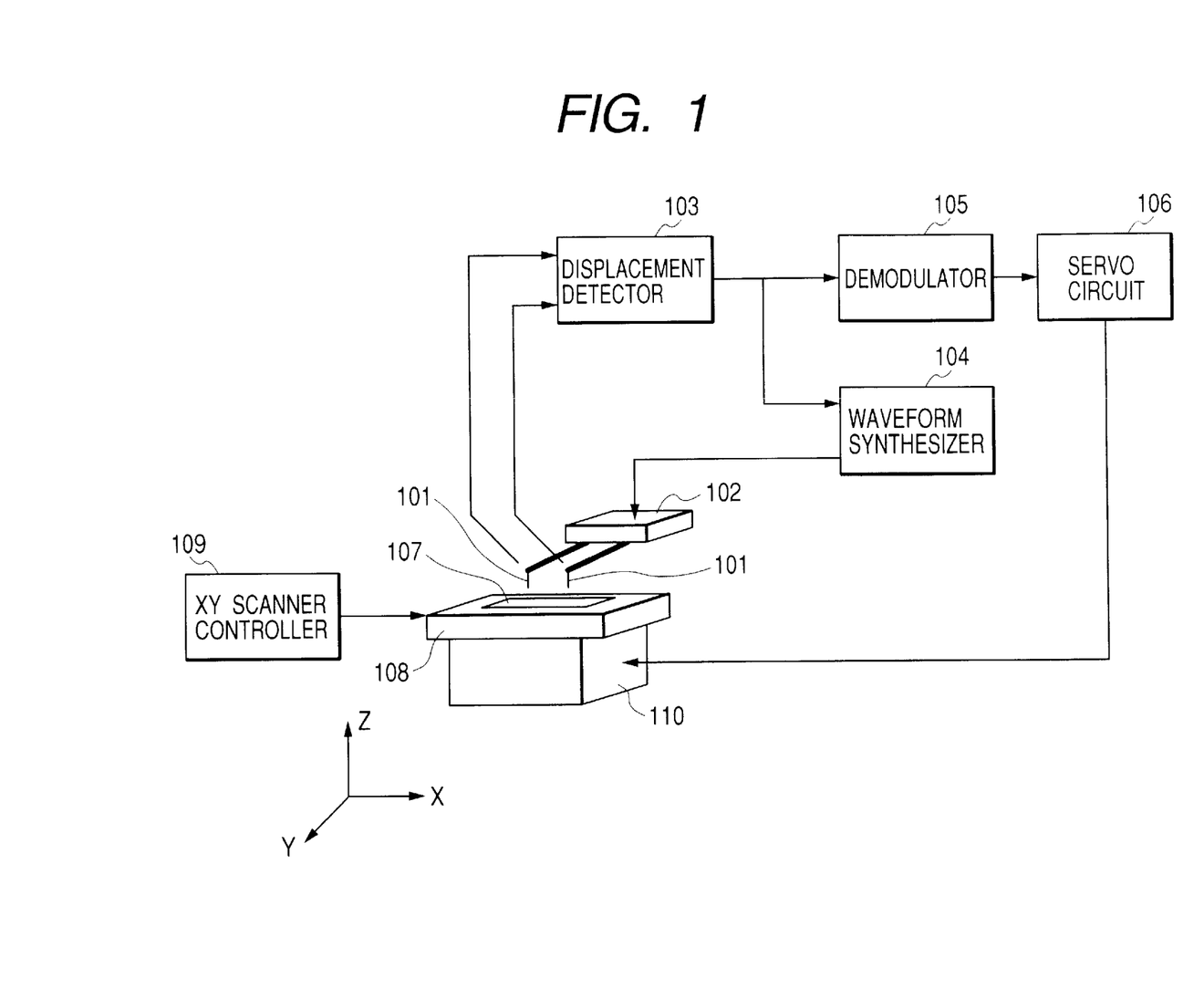
FIG. 1 is a block diagram schematically illustrating the configuration of a non-contact-type atomic microscope, which is an embodiment of the present invention.

FIG. 1 is a block diagram schematically illustrating the configuration of a non-contact-type atomic microscope, which is an embodiment of the present invention. Referring to FIG. 1, this non-contact-type atomic microscope comprises a multiprobe 101 consisting of a plurality of probes, an actuator 102 for vibrating the multiprobe 101 at the same time, a displacement detector 103 for detecting any displacement (amplitude) of each probe of the multiprobe 101, a demodulator 105 for demodulating output signals of the displacement detector 103 (signals resulting from the detection of displacement of the probes) by a prescribed demodulating method and supplying a signal corresponding to the surface shape of a sample 107, a waveform synthesizer 104 for adding output waveforms corresponding to the displacements of the different probes supplied from the displacement detector 103 and applying the sum to the actuator 102, a scanner 108 on which the sample 107 is to be mounted, a piezo element (also known as a stack piezo) 110 for shifting the scanner 108 in a direction normal to its sample arranging surface (the Z direction in FIG. 1), a servo circuit 106 for controlling the shifting of the scanner 108 by the piezo element 110, and an XY scanner controller 109 for controlling the scanner 108 in the intra-facial direction of sample mounting surface (the XY direction in FIG. 1).

Each of the probes constituting the multiprobe 101 is intentionally deviated from others in resonance point. In this mode of implementing the invention, each of the probes constituting the multiprobe 101 is vibrated by the common actuator 102. While a common actuator can be used to vibrate all the probes constituting the multiprobe 101 as in this case, if the number of probes increases beyond a certain level, the probes constituting the multiprobe can as well be divided into several groups and an actuator is provided for vibration of each group. While the actuator 102 may be configured of a piezoelectric element or the like, which is well known, it should have at least a vibration range (frequency range in which vibration is possible) that can well cover the resonance frequency of each of the probes constituting the multiprobe 101 which are to be vibrated.

The method of detection by the displacement detector 103 differs with the probe configuration of the multiprobe 101. If, for instance, cantilevered probes are used, the tip of each probe is irradiated with light, and the behavior of the probe is known from the displacement of the resultant reflected light. Or if probes configured of piezo resistance elements are used, the probes are biased, and the displacement (amplitude) of each probe is known from a variation in resistance accompanying the flexure of the probe. Some other detecting methods are also available for use.

Although the demodulator 105 here is configured of a demodulating circuit, typically an AM demodulating circuit or an FM demodulating circuit, some other demodulating method can as well be used. On the basis of signals demodulated by this demodulator 105, the surface shape of the sample 107 undergoes image processing.

The servo circuit 106, whose input is the output of the demodulator 105, subjects the scanner 108 to feedback control in the Z direction. More specifically, the servo circuit 106 controls the distance (spacing) between the sample 107 and the multiprobe 101 on the basis of the output of the demodulator 105 to prevent the multiprobe 101 from being destroyed, or the sample 107 from being damaged, by contact between the sample 107 and the multiprobe 101.

The configuration of the waveform synthesizer 104, configured mainly of an adder, differs with the configuration of the demodulating circuit in the demodulator 105. Details will be given afterwards.

Next will be described the operation of this non-contact-type atomic microscope.

The multiprobe 101 causes the scanner 108 to scan the surface of the sample 107 mounted thereon by shifting the scanner 108 in the XY direction. This shifting of the scanner 108 in the XY direction is controlled by the XY scanner controller 109. Any unevenness of the surface of the sample 107 is observed by such a scanning method.

When observing the surface of the sample 107, as described earlier, the signals of the probes regarding the surface shape of the sample 107 are detected from the output waveforms of the displacement detector 103 by the demodulating circuit of the demodulator 105, and the servo circuit 106, referencing these detection signals, aligns the multiprobe 101 and the sample 107 so that they may not come into contact with each other. This results in keeping constant the distance between the multiprobe 101 and the sample 107, and the scanner 108 is caused to perform scanning in this state.

During the scanning process, each of the probes constituting the multiprobe 101 is vibrated by the common actuator 102 at a frequency of or near its resonance point. Information on the surface shape of the sample 107 is detected by the displacement detector 103 as a signal corresponding to the deviation of the resonance point of each of the probes constituting the multiprobe 101, and this detection signal is entered into the waveform synthesizer 104 and the demodulator 105. The waveform synthesizer 104 generates a synthetic waveform synthesized from the vibration signal waveforms of the probes generated on the basis of signals corresponding to the resonance points or deviations from the resonance points of the probes supplied from the displacement detector 103, and the synthetic waveform is supplied to the actuator 102. The application of this synthetic waveform results in vibration of each of the probes constituting the multiprobe 101 at a frequency of or near its resonance point.

The method of vibrating each of the probes constituting the multiprobe 101 at a frequency of or near its resonance point will be described below.

Each of the probes constituting the multiprobe 101 has its own sensitivity distribution, and achieves its maximum amplitude at its resonance point. Therefore, by appropriately setting the resonance point of each probe, its sensitivity distribution functions as something like a so-called band pass filter. This results in outputting from the waveform synthesizer 104 a synthetic signal having a component of or near the resonance frequency of each probe and, even when the multiprobe 101 is vibrated, in each probe a component of or near its resonance point is selected, so that each probe is vibrated at a frequency of or near its resonance point.

Since each of the probes constituting the multiprobe 101 can be vibrated at a frequency of or near its resonance point using a common actuator in this mode of implementing the invention as described above, unevenness in detection sensitivity among the individual probes constituting the multiprobe 101 can be restrained, resulting in more accurate observation results.

The waveform synthesizer 104 generates vibration signals for individual probes basically according to the output signal of the displacement detector 103, and synthesizes them to generate a synthetic signal having a component of or near the resonance frequency of each probe. The procedure of generating the synthetic signal differs with the demodulating system. Two embodiments of the invention, one using AM detection and the other using FM detection, will be described below as specific examples.

(First Embodiment: AM Detection)

Figure 2:
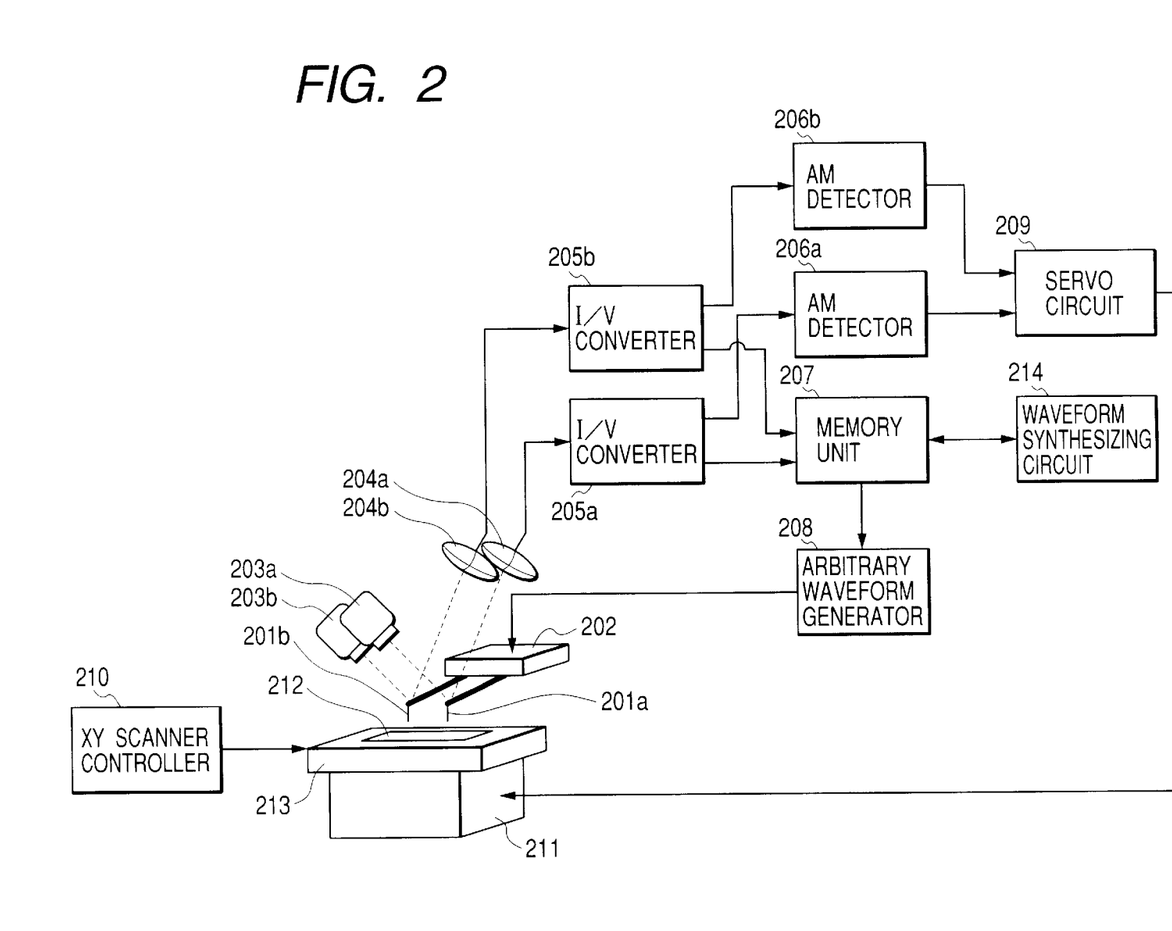
FIG. 2 is a block diagram schematically illustrating the configuration of a non-contact-type atomic microscope, which is a first embodiment of the invention.

FIG. 2 is a block diagram schematically illustrating the configuration of a non-contact-type atomic microscope, which is a first embodiment of the present invention. In this non-contact-type atomic microscope is used an actuator 202 consisting of a piezoelectric ceramic material and a cantilevered multiprobe consisting of probes 201a and 201b. The probes 201a and 201b have a Q value, representing the acuity of the vibration system, of 400 in the atmosphere and resonance frequencies of 10 kHz and 300 kHz, respectively.

Its displacement detecting units, using optical levers, are separately provided for the probes 201a and 201b. They consist of laser diodes 203a and 203b, quadrant photodiodes 204a and 204b, and I/V converters 205a and 205b. A laser beam from the laser diode 203a is reflected by a prescribed portion of the probe 201a, and the reflected light comes incident on the quadrant photodiode 204a. As the probe 201a vibrates, the output of the quadrant photodiode 204a varies with the amplitude of the vibration. The output of the quadrant photodiode 204a (amperage signal) is converted by the I/V converter 205a into a voltage signal. The laser diode 203b, the quadrant photodiode 204b and the I/V converter 205b are similarly configured, providing a voltage signal corresponding to the amplitude of the probe 201b.

An XY scanner 213 on which a sample 212 is mounted is controlled by an XY scanner controller 210 in its shifting in the XY direction. This XY scanner 213 can also be shifted in the Z direction by a stack piezo 211, and this shifting in the Z direction is controlled by a servo circuit 209. These controls by the XY scanner controller 210 in the XY direction and by the servo circuit 209 in the Z direction are the same as described above referring to the mode of implementing the invention, and are not described in detail.

Figure 4:
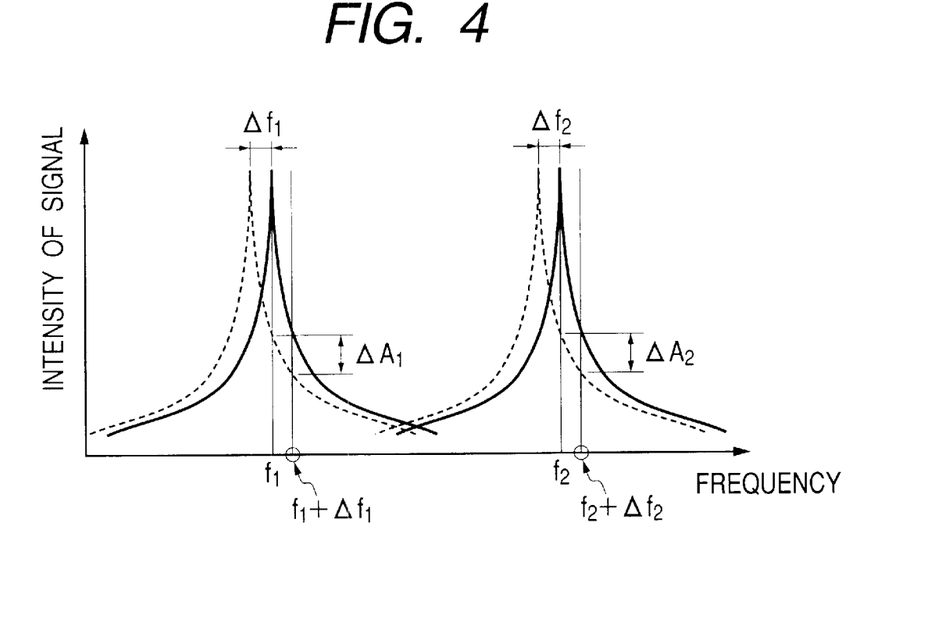
FIG. 4 shows resonance frequencies and vibration displacements of different probes in the non-contact-type atomic microscope illustrated in FIG. 2.

The demodulator is composed of AM detectors 206a and 206b. Into the AM detector 206a is entered the output of the I/V converter 205a, and into the AM detector 206b, that of the I/V converter 205b. In the AM detection by these AM detectors 206a and 206b, as shown in FIG. 4 for instance, the amplitude of the vibration of each probe of the multiprobe at the vibrating frequency, vibrated at a point ($f_1+\Delta f_1$ or $f_2+\Delta f_2$) deviated by $\Delta f$ ($\Delta f_1=25$ Hz or $\Delta f_2=750$ Hz) from its resonance point ($f_1=10$ kHz or $f_2=300$ kHz), is detected, and a variation in the resonance frequency of each probe due to the physical interaction between the sample 212 and the probe is detected as an intensity variation $\Delta A$ of the signal.

In carrying out AM detection as described above, it is necessary to keep each of the probes 201a and 201b vibrated at a constant frequency ($f_1+\Delta f_1$ or $f_2+\Delta f_2$) all the time. In this embodiment of the invention, in order to determine this vibrating frequency, the waveform synthesizer is composed of a waveform synthesizing circuit 214, a memory unit 207, and an arbitrary waveform generator 208. The memory unit 207 detects the resonance frequency of each of the probes 201a and 201b from the amplitude signal of each probe supplied from the I/V converter 205a or 205b on the basis of, for instance, a peak value, and stores it. It further generates a signal resulting from the shifting of the amplitude signal of each probe by an equivalent of a prescribed frequency from the resonance frequency. The waveform synthesizing circuit 214 synthetically computes signals resulting from the shifting of the resonance frequencies of the probes, supplied by the memory unit 207, by respectively prescribed frequencies. The memory unit 207 stores this result of computation. The arbitrary waveform generator 208 generates a drive signal on the basis of the synthetic signal stored in the memory unit 207, and applies it to the actuator 202. It also generates a drive signal for the actuator 202 required for figuring out the resonance frequency of each probe, and applies it to the actuator 202.

Next will be described in specific terms the operation of the non-contact type atomic microscope embodying the invention as described above.

First, before observing the sample 212, the probes 201a and 201b are shifted to a region where no atomic force from the sample 212 can reach. Then, the frequency of the signal applied from the arbitrary waveform generator 208 to the actuator 202 is swept over a prescribed frequency range to vibrate the actuator 202 and thereby to vibrate the multiprobe. The probes 201a and 201b, as each has its natural resonance frequency, manifest their respective maximum amplitudes of vibration when the vibration frequency of the actuator 202 coincides with the respective resonance frequencies of the probes. The memory unit 207 detects and stores the frequency at which each of the probes 201a and 201b has manifested its maximum amplitude of vibration (resonance frequency).

Upon completion of the frequency sweeping by the arbitrary waveform generator 208, the memory unit 207 supplies signal waveforms resulting from shifting of the resonance frequency f ($f_1$, $f_2$) of the probes 201a and 201b by respectively prescribed frequencies Δf ($\Delta f_1$=25 Hz and $\Delta f_2$=750 Hz). The waveform synthesizing circuit 214 synthesizes a signal waveform having these shifted frequencies ($f_1+\Delta f_1$ and $f_2+\Delta f_2$), referencing the outputs of the I/V converters 205a and 205b, if necessary, and generates a signal for driving the actuator 202 during observation.

During observation, the probe 201a of the multiprobe is vibrated at the frequency of ($f_1+\Delta f_1$) all the time on the basis of the synthetic waveform (containing the frequency components of $f_1+\Delta f_1$ and $f_2+\Delta f_2$) stored in the memory unit 207, and the probe 201b is vibrated at the frequency of ($f_2+\Delta f_2$) all the time. In this vibrated state, the multiprobe is brought close to and caused to scan the surface of the sample 212, and detects amplitude variations of the probes according to the unevenness of the surface as described below.

When the probe 201a comes to a convex portion of the sample (approaches the sample surface), the resonance frequency of the probe 201a shifts in the descending direction, and the vibration amplitude of the probe narrows. On the other hand, when the probe 201a comes to a concave portion of the sample (moves away from the sample surface), the resonance frequency of the probe 201a shifts in an ascending direction, and the vibration amplitude of the probe widens. In this way, the unevenness of the sample surface can be observed by detecting variations in the resonance frequencies of the probes as variations in signal intensity.

The non-contact-type atomic microscope embodying the invention in this manner, with both the probes 201a and 201b, can observe the unevenness of the sample surface at a resolution of approximately 10 nm.

Although in the configuration described above the result of computation by the waveform synthesizing circuit 214 is temporarily stored in the memory unit 207 and the memory unit 207 is caused to supply the synthetic waveform to be entered into the arbitrary waveform generator 208, it is also possible to enter the synthetic waveform from the waveform synthesizing circuit 214 directly into the arbitrary waveform generator 208 to drive the actuator 202.

(Second Embodiment: FM Detection)

Figure 3:
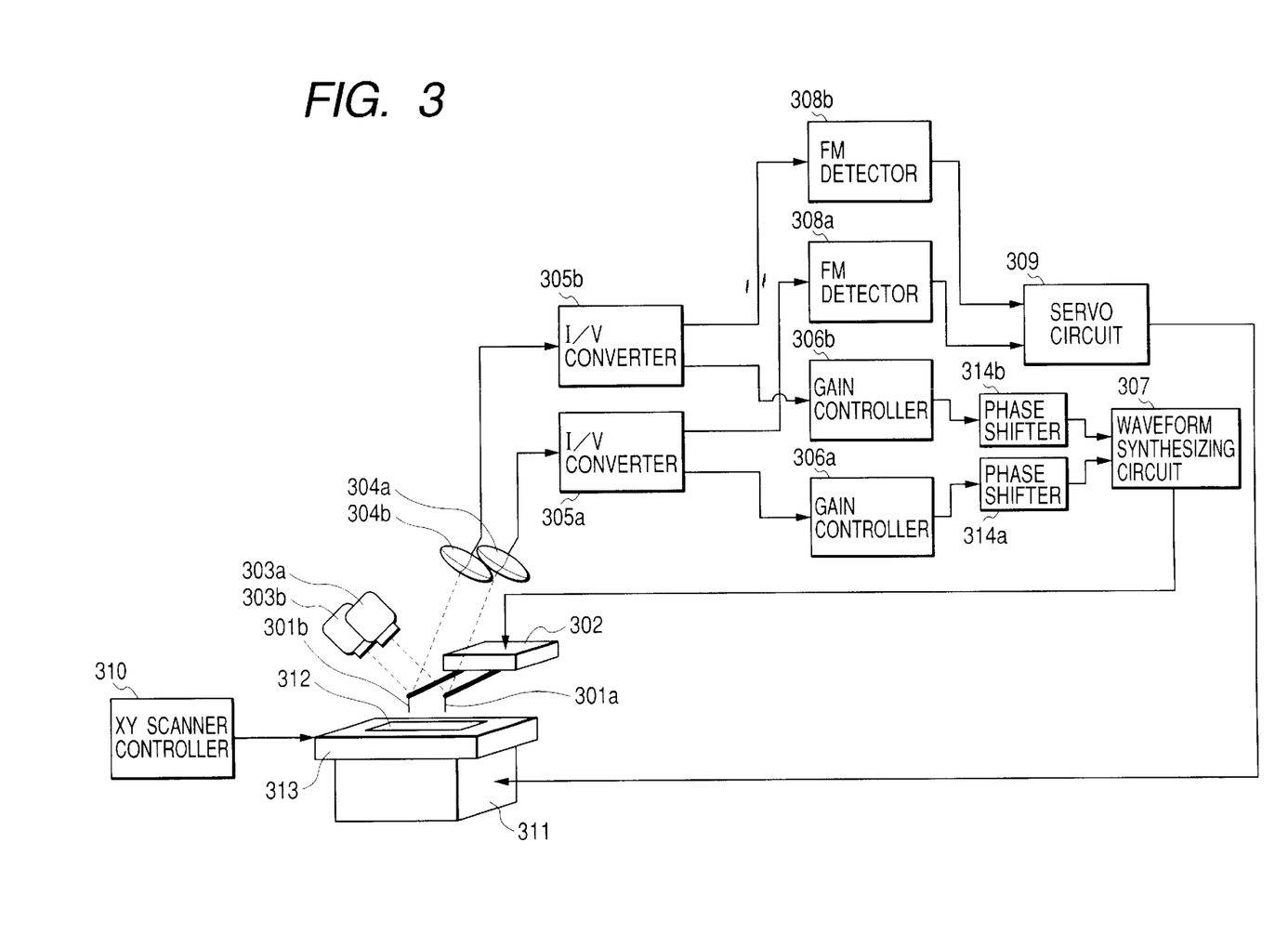
FIG. 3 is a block diagram schematically illustrating the configuration of a non-contact-type atomic microscope, which is a second embodiment of the invention.

FIG. 3 is a block diagram schematically illustrating the configuration of a non-contact-type atomic microscope, which is a second embodiment of the invention.

In this non-contact-type atomic microscope are used an actuator 302 consisting of a piezoelectric ceramic material and a cantilevered multiprobe consisting of probes 301a and 301b. Both the probes 301a and 301b have a Q value, representing the acuity of the vibration system, of 400 in the atmosphere and resonance frequencies of 10 kHz and 300 kHz, respectively. Its displacement detecting units, using optical levers, are separately provided for the probes 301a and 301b. They consist of laser diodes 303a and 303b, quadrant photodiodes 304a and 304b, and I/V converters 305a and 305b. An XY scanner 313 on which a sample 312 is mounted is controlled by an XY scanner controller 310 in its shifting in the XY direction. This XY scanner 313 can also be shifted in the Z direction by a stack piezo 311, and this shifting in the Z direction is controlled by a servo circuit 309. The configuration described here is substantially similar to that of the first embodiment described above.

In this embodiment, each of the I/V converters 305a and 305b is provided with a band pass filter. The center frequency of the band pass filter of the I/V converter 305a is set in the vicinity of the resonance frequency of the probe 301a, and that of the band pass filter of the I/V converter 305b is set in the vicinity of the resonance frequency of the probe 301b.

Figure 5:
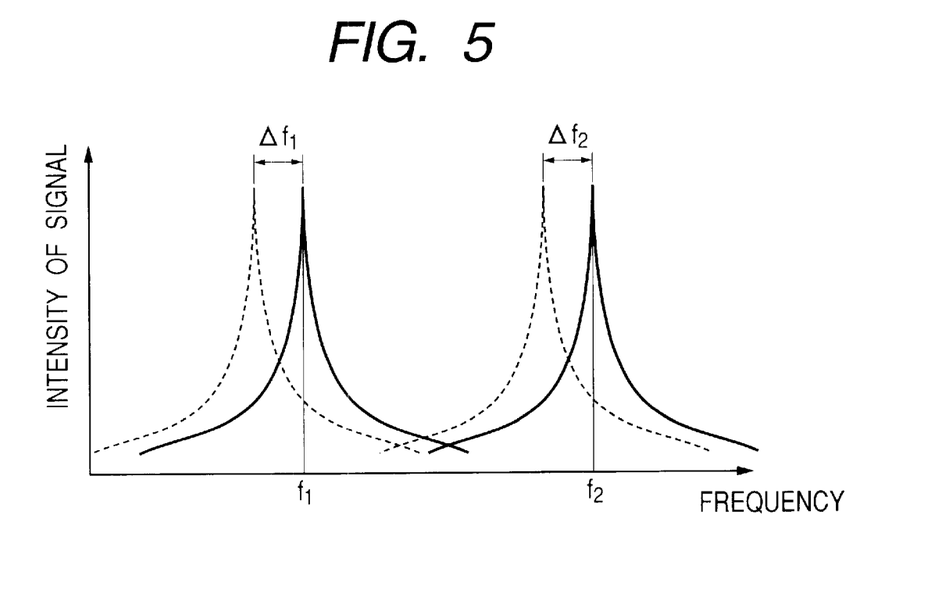
FIG. 5 schematically shows deviations of resonance frequencies of different probes in the non-contact-type atomic microscope shown in FIG. 3.

The demodulator consists of FM detectors 308a and 308b. Into the FM detector 308a is entered the output signal of the I/V converter 305a, and into the FM detector 308b is entered the output signal of the I/V converter 305b. In the FM detection by these FM detectors 308a and 308b, as shown in FIG. 5 for instance, deviations in the resonance frequencies of the probes 301a and 301b from their resonance points ($f_1$ and $f_2$) due to the physical interaction between the sample 312 and the probes 301a and 301b are detected as Δf. The example shown in this FIG. 5 represents resonance frequency deviations of the probes 301a and 301b when both have shifted in the direction of approaching the sample surface.

The waveform synthesizer consists of auto gain controllers 306a and 306b, phase shifters 314a and 314b, and a waveform synthesizing circuit 307. The gain controllers 306a and 306b are provided on the output lines of the I/V converters 305a and 305b, respectively, and carry out automatic gain adjustment so that the output waveforms of the I/V converters maintain constant amplitudes all the time. The waveform synthesizing circuit 307 synthesizes the output waveforms of the gain controllers 306a and 306b to supply a drive signal for the actuator 302. The phase shifters 314a and 314b adjust the output phases of the I/V converters so that the probes 301a and 301b can maintain vibrations at the respective resonance frequencies shifted to correspond to their distances from the sample surface, and performs forward control. This configuration enables the probes 301a and 301b to be vibrated by the actuator 302 all the time at the respective resonance frequencies shifted to correspond to their distances from the sample surface, resulting in an apparently improved probe sensitivity and making possible highly sensitive detection of resonance frequency variations.

In this embodiment, when the probe 301a comes to a convex portion of the sample (approaches the sample surface), the resonance frequency of the probe 301a shifts in the direction of falling below $f_1$, and the actuator 302 vibrates the probe 301a at this shifted frequency. Thus the probe 301a, as its resonance frequency is shifted by unevenness of the sample surface, is vibrated at the shifted resonance frequency. Observation of the unevenness of the sample surface can be accomplished by figuring out the difference between the resonance frequency $f_1$ of the probe 301a in a predetermined reference position (a position where the distance between the probe and the sample surface is known in advance) and the shifted resonance frequency (shift quantity).

The non-contact-type atomic microscope embodying the invention in this manner, with both the probes 301a and 301b, can observe the unevenness of the sample surface at a resolution of approximately 10 nm.

As hitherto described, in ncAFM using a multiprobe, all the probes can be vibrated at a frequency of or near its resonance point according to the present invention, making possible observation at a high level of sensitivity. As sensitivity disparities among different probes can be restrained at the same time, fluctuations in the resolution of the observed image can also be restrained, making it possible to extensively obtain satisfactory observed images well reflecting the surface shape of the sample.

There is the additional advantage of enhanced working efficiency because the measuring personnel need not align the resonance points of different probes.

What is claimed is:

1. A non-contact-type atomic microscope comprising:
   a plurality of probes differing in resonance frequency;
   an actuator for vibrating said plurality of probes simultaneously; and a drive signal generating circuit for generating a drive signal for said actuator, the drive signal containing a predetermined frequency for vibrating each of said plurality of probes.

2. The non-contact-type atomic microscope, as set forth in claim 1, further comprising:

a displacement detector for detecting any displacement of said probes, wherein said drive signal generating circuit generates the drive signal based on an output signal for each probe supplied from said displacement detector.

3. The non-contact-type atomic microscope, as set forth in claim 2, wherein said drive signal generating circuit shifts a waveform of the output signal of each of said probes by an equivalent of a prescribed frequency, and further has a waveform synthesizing circuit for generating a synthetic waveform resulting from synthesis of such waveforms, a memory unit for storing the synthetic waveform, and an arbitrary waveform generating unit for generating a drive signal to be applied to said actuator based on the synthetic waveform stored in said memory unit.

4. The non-contact-type atomic microscope, as set forth in claim 2, wherein said drive signal generating circuit has a gain controller for keeping constant an amplitude of the output signal of each of said probes, a phase shift circuit for adjusting the phase of the output signal of each probe having undergone gain adjustment by said gain controller, and a waveform synthesizing circuit for synthesizing the output signals of the probes having undergone the phase adjustment and generating a drive signal to be applied to said actuator.

5. An observation method for observing a surface shape of a sample by using a plurality of probes, comprising:

a step of vibrating the plurality of probes simultaneously with a common actuator;

wherein a signal for driving the actuator contains a predetermined frequency for vibrating each of the probes;

a step of detecting any displacement in each of the probes and generating an output signal; and a step of generating a signal representing the surface shape based on the output signal.

6. The observation method, as set forth in claim claim 5, wherein the signal representing the surface shape is generated based on amplitude variations of the output signal.

7. The observation method, as set forth in claim 5, wherein the signal representing the surface shape is generated based on resonance frequency variations of the output signal.

* * * * *

UNITED STATES PATENT AND TRADEMARK OFFICE
CERTIFICATE OF CORRECTION

PATENT NO. : 6,684,686 B2
DATED : February 3, 2004
INVENTOR(S) : Takeaki Itsuji et al It is certified that error appears in the above-identified patent and that said Letters Patent is hereby corrected as shown below:

Column 1,
Line 22, "(ScaM)" should read -- (ScaM), --; and
Line 23, "(SNOM)" should read -- (SNOM), --.

Column 3,
Line 11, "frequencies;" should read -- frequencies, --.

Column 5,
Line 51, "is used" should read -- are used --.

Column 8,
Line 27, "performs" should read -- perform --.

Column 10,
Line 10, "actuator;" should read -- actuator, --; and
Line 19, "claim claim 5," should read -- claim 5, --.

Signed and Sealed this

Seventh Day of September, 2004

JON W. DUDAS
*Director of the United States Patent and Trademark Office*